United States Patent
Yang et al.

(10) Patent No.: US 11,401,238 B2
(45) Date of Patent: Aug. 2, 2022

(54) CARBON DIOXIDE-REVERSIBLY-PROTECTED CHAIN EXTENSION-CROSSLINKING AGENT AND PREPARATION METHOD AND USE THEREOF

(71) Applicant: Changchun Institute of Applied Chemistry, Chinese Academy of Sciences, Changchun (CN)

(72) Inventors: Xiaoniu Yang, Changchun (CN); Bo Zhang, Changchun (CN); Xiaoli Zhao, Changchun (CN); Xiaoxiao Li, Changchun (CN); Yumeng Tian, Changchun (CN)

(73) Assignee: CHANGCHUN INSTITUTE OF APPLIED CHEMISTRY, CHINESE ACADEMY OF SCIENCES, Changchun (CN)

( * ) Notice: Subject to any disclaimer, the term of this patent is extended or adjusted under 35 U.S.C. 154(b) by 0 days.

(21) Appl. No.: 16/473,776

(22) PCT Filed: Feb. 2, 2019

(86) PCT No.: PCT/CN2019/074634
§ 371 (c)(1),
(2) Date: Jun. 26, 2019

(87) PCT Pub. No.: WO2020/057047
PCT Pub. Date: Mar. 26, 2020

(65) Prior Publication Data
US 2021/0332006 A1    Oct. 28, 2021

(30) Foreign Application Priority Data

Sep. 21, 2018 (CN) .......................... 201811104976.8

(51) Int. Cl.
*C08G 18/32* (2006.01)
*C07C 269/04* (2006.01)
(Continued)

(52) U.S. Cl.
CPC ........ *C07C 269/04* (2013.01); *C08G 18/0871* (2013.01); *C08G 18/10* (2013.01);
(Continued)

(58) Field of Classification Search
CPC .................................................. C07C 269/04
See application file for complete search history.

(56) References Cited

U.S. PATENT DOCUMENTS 3,029,227 A    4/1962    Robb
3,406,131 A  * 10/1968   Gowecke ............... C08G 59/52
                                                   521/178

(Continued)

FOREIGN PATENT DOCUMENTS

CN    104592058 A    5/2015
EP    2 410 230 A1   1/2012

OTHER PUBLICATIONS

International Search Report and the Written Opinion of the International Searching Authority as issued in International Patent Application No. PCT/CN2019/074634, dated Jun. 21, 2019.

(Continued)

*Primary Examiner* — Michael L Leonard
(74) *Attorney, Agent, or Firm* — Pillsbury Winthrop Shaw Pittman LLP

(57) ABSTRACT

Carbon dioxide-reversibly-protected chain extension-crosslinking agents and a preparation method and use thereof are disclosed, The carbon dioxide-reversibly-protected chain extension-crosslinking agents have chemical structures represented by Formula I, Formula II, Formula III or Formula IV, wherein, n, m and p are integers, R is either $OCH_2CH(CH_3)$ or $OCH_2CH_2$, $1 \leq n \leq 20$, $1 \leq m \leq 10$, and $1 \leq p \leq 10$.

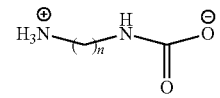

Formula I

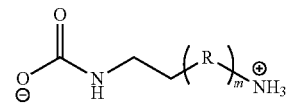

Formula II

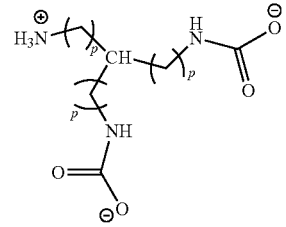

Formula III

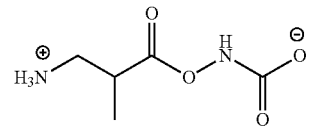

Formula IV

16 Claims, No Drawings

(51) Int. Cl.
*C08G 18/08* (2006.01)
*C08G 18/10* (2006.01)
*C08G 18/38* (2006.01)
*C07C 271/02* (2006.01)

(52) U.S. Cl.
CPC ..... *C08G 18/3265* (2013.01); *C08G 18/3268* (2013.01); *C08G 18/3823* (2013.01); *C07C 271/02* (2013.01)

(56) References Cited

U.S. PATENT DOCUMENTS

| | | | |
|---|---|---|---|
| 3,635,908 A | | 1/1972 | Vogt et al. |
| 4,600,652 A | * | 7/1986 | Solomon ............... C08G 18/84 523/112 |
| 5,124,447 A | * | 6/1992 | Squiller ............... C08G 18/10 528/68 |
| 5,189,205 A | * | 2/1993 | McGhee ............... C07C 263/04 560/345 |

OTHER PUBLICATIONS

Schauenburg, D., et al., "Covalently functionalized amide cross-linked hydrogels from primary amines and polyethylene glycol acyltrifluoroborates (PEG-KATs)," Journal of Materials Chemistry B. 26.6, 2018, (Jun. 26, 2018).

Alauzun, J., et al., "Reversible Covalent Chemistry of $CO_2$: An Opportunity for Nano-Structured Hybrid Organic-Inorganic Materials," *Chem. Mater.* 2008, 20, pp. 503-513, Dec. 2007.

\* cited by examiner

CARBON DIOXIDE-REVERSIBLY-PROTECTED CHAIN EXTENSION-CROSSLINKING AGENT AND PREPARATION METHOD AND USE THEREOF

This application is the U.S. national phase entry of PCT patent application no. PCT/CN2019/074634, which was filed on Feb. 2, 2019, which claims the benefit of priority of Chinese Patent Application No. 201811104976.8, which was filed on Sep. 21, 2018.

TECHNICAL FIELD

The present disclosure pertains to the technical field of chain extension-crosslinking agents, and particularly relates to carbon dioxide-reversibly-protected chain extension-crosslinking agents and a preparation method and use thereof, especially use of the chain extension-crosslinking agents in the preparation of polyurethanes.

BACKGROUND

Polyurethane elastomers have high wear resistance, high carrying capacity, excellent cutting and wearing resistance, wide hardness range, and ozone degradation resistance, as well as excellent properties such as portability and castability. As compared to other plastic materials, polyurethanes are non-brittle and more wear resistant, and have good elasticity memory. Thus, they can be used for various products, such as airplane hangers, liners, star wheels, gaskets, impellers, and gears. Polyurethane elastomers can be classified into casting type, thermoplastic type, reaction injection molding type, kneading type and the like depending on their product manufacture methods. Here, the polyurethane elastomer of casting type is formed by converting a liquid to a solid via a reaction. It may be produced by a one-pot process or two-step process. The product molding may be performed through pressurized vulcanization or normal pressure vulcanization, or through heat vulcanization, or room temperature curing. The cast molding may be performed manually or with a casting machine continuously. The diversity of cast molding processes provides convenience for medium- and large-scale preparation of elastomers.

The raw materials for polyurethane elastomers of a casting type mainly comprise three types, i.e., oligomeric polyols, polyisocyanates, and chain extension-crosslinking agents. The oligomeric polyols mainly comprise polyester polyols, polyether polyols, polycarbonate polyols, polymeric polyols and the like. The polyisocyanates comprise toluene diisocyanate (TDI), diphenylmethane diisocyanate (MDI), 1,5-naphthalene diisocyanate (NDI), p-phenylene diisocyanate (PPDI) and the like. The chain extension-crosslinking agents comprise chain-extending agents (i.e. chain extenders), chain extension-crosslinking agents, and crosslinking agents. The chain extension-crosslinking agents are typically some small molecule diamines, polyols, or polyamines, wherein the diamines are important chain extension-crosslinking agents for polyurethanes of the casting type. Aliphatic polyamines have strong alkalinity and high activity, and can react with isocyanate rapidly, resulting in a high gelation rate. Therefore, aliphatic polyamines are difficult to be used in the production of polyurethane elastomers, and mainly used in the production of spray coating polyesters, polyureas and epoxy resins. Introducing electron withdrawing groups or steric hindered groups into the aromatic ring reduces the reactivity of the amino groups and makes their activity relatively moderate, and in this way they can be applied to produce polyurethane elastomers. At present, 3,3'-dichloro-4,4'-diaminodiphenylmethane (MOCA) as an aromatic compound is mostly used. However, it is toxic to a certain extent, and suffers from the problems of strict use conditions, short pot life and the like. Other types of chain extenders also suffer from the problems of different properties, complex synthesis steps, and the like.

SUMMARY

An object of the present disclosure is to solve a technical problem that the reaction between polyamines and isocyanates are too fast to be used to synthesize polyurethane elastomers, and thus to provide carbon dioxide-reversibly-protected chain extension-crosslinking agents and a preparation method and use thereof.

Technical solutions used for solving the technical problem mentioned above are as follows.

The present disclosure provides a carbon dioxide-reversibly-protected chain extension-crosslinking agent having a chemical structure represented by Formula I, Formula II, Formula III, or Formula IV:

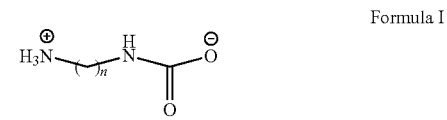

Formula I

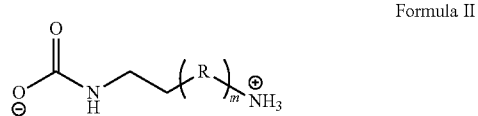

Formula II

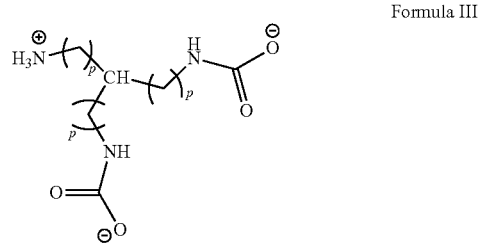

Formula III

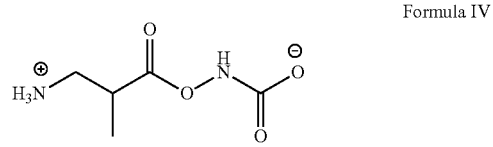

Formula IV where in Formula I, Formula II, and Formula III, n, m and p are integers, R is either $OCH_2CH(CH_3)$ or $OCH_2CH_2$, $1 \leq n \leq 20$, $1 \leq m \leq 10$, and $1 \leq p \leq 10$.

The present disclosure also provides a preparation method of a carbon dioxide-reversibly-protected chain extension-crosslinking agent, the method comprising: dissolving aliphatic diamine or aliphatic triamine in an organic solvent to obtain a reaction mixture, and stirring the reaction mixture under an atmosphere of carbon dioxide to obtain the carbon dioxide-reversibly-protected chain extension-crosslinking agent. The aliphatic diamine is aliphatic alkane diamine, aliphatic ether diamine or aliphatic ester diamine, and the aliphatic triamine is aliphatic alkane triamine. The molar ratio of the carbon dioxide to the aliphatic diamine or the aliphatic triamine is in a range of 1~2:1.

Preferably, the atmosphere of carbon dioxide is a carbon dioxide gas at a flow rate of 1-20 ml/min.

Preferably, the reaction temperature is 0-35° C.

Preferably, the aliphatic polyamine is aliphatic triamine or aliphatic diamine with 6 carbon atoms or less, and the reaction temperature is 0-10° C.

Preferably, the aliphatic diamine is aliphatic alkane diamine, aliphatic ether diamine or aliphatic ester diamine, and the aliphatic triamine is aliphatic alkane triamine. More preferably, the aliphatic alkane diamine is ethylenediamine, 1,6-hexanediamine, or 1,10-decanediamine; the aliphatic ether diamine is 2,2'-oxybis(ethylamine), 2,2'[1,2-ethylenedi(oxy)]bis-ethylamine, 2,2'-[oxybis(2,1- ethyleneoxy)]bis-ethylamine, or 1-(2-aminoethoxy)propan-2-amine; the aliphatic ester diamine is 1-amino-2-propyl carbamate; and the aliphatic alkane triamine is N,N-bis(aminomethyl)-methanediamine, N,N-bis(2-aminoethyl)-1,2-ethylenediamine, or N,N-bis(4-aminobutyl)-1,4-butanediamine.

Preferably, the aliphatic polyamine is aliphatic alkane diamine, the stirring speed is 100-300 rpm, and the reaction time is 5-30 min; or the aliphatic polyamine is aliphatic ether diamine, aliphatic ester diamine or aliphatic triamine, the stirring speed is 100-400 rpm, and the reaction time is 20-60 min. The faster the stirring speed and the longer the reaction time, the reaction between carbon dioxide and aliphatic polyamine is more complete.

The present disclosure also provides use of the carbon dioxide-reversibly-protected chain extension-crosslinking agent mentioned above in the preparation of polyurethane material.

Preferably, the steps are as follows:

step I: adding an oligomeric polyol with a molecular weight of 1000-3000 to a reactor, dewatering it under vacuum, adding a diisocyanate under the protection of an inert atmosphere, and heating the resultant mixture to 70-130° C. and reacting them, to obtain a polyurethane prepolymer with an NCO content of 3%-9% as desired;

step II: dispersing the carbon dioxide-reversibly-protected chain extension-crosslinking agent in an organic solvent to obtain a dispersion, adding the dispersion to the polyurethane prepolymer, mixing them evenly, and then removing the organic solvent to obtain a mixture; and step III: reacting the mixture obtained in step II at 80-200° C. for 5-120 min, curing and molding the mixture to obtain a polyurethane.

Preferably, in step I, the oligomeric polyol is one or more selected from a polyester polyol, a polyether polyol, a polycarbonate polyol, and a polymeric polyol.

Preferably, in step I, the isocyanate is one or more selected from toluene diisocyanate (TDI), diphenylmethane diisocyanate (MDI), 1,5-naphthalene diisocyanate (NDI), and p-phenylene diisocyanate (PPDI).

Preferably, in step I, the oligomeric polyol is dewatered under a vacuum of 50-500 Pa at a temperature of 120° C.-140° C.

Preferably, in step II, the condition for mixing evenly is stirring at 100-300 rpm for 10-30 min.

DETAILED DESCRIPTION

In order to make the present disclosure clearer and more apparent, the present disclosure will be further described in detail below with reference to particular embodiments. It should be noted that the particular embodiments described here are only intended to explain, instead of limiting the claims of the present disclosure.

The carbon dioxide-reversibly-protected chain extension-crosslinking agents of the present disclosure have structure formulae as represented by Formula I, Formula II, Formula III, or Formula IV:

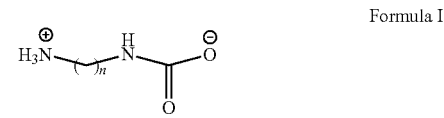

Formula I

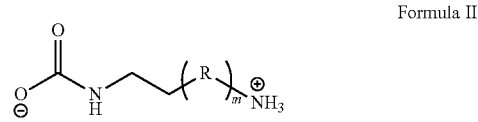

Formula II

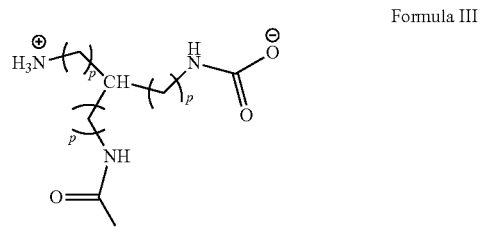

Formula III

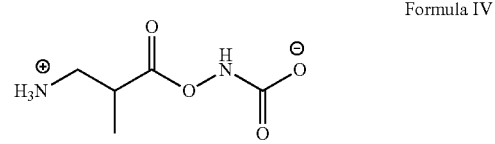

Formula IV where in Formula I, Formula II, and Formula III, n, m and p are integers; R is either $OCH_2CH(CH_3)$ or $OCH_2CH_2$; $1 \leq n \leq 20$, preferably $2 \leq n \leq 15$, and more preferably $2 \leq n \leq 10$; $1 \leq m \leq 10$, preferably $1 \leq m \leq 5$, and more preferably $1 \leq m \leq 3$; and $1 \leq p \leq 10$, preferably $1 \leq p \leq 6$, and more preferably $1 \leq p \leq 5$.

In the present disclosure, the phrase "reversibly-protected" in the term "carbon dioxide-reversibly-protected chain extension-crosslinking agents" means that polyamines lose their activities by reacting with carbon dioxide to produce ammonium carboxylate, and the ammonium carboxylate can release the original active polyamines under a heating condition.

The present disclosure also provides a preparation method of a carbon dioxide-reversibly-protected chain extension-crosslinking agent, the method comprising: dissolving aliphatic diamine or aliphatic triamine with 20 carbon atoms or fewer in an organic solvent to obtain a mixture, and stirring and reacting the mixture under an atmosphere of carbon dioxide to obtain the carbon dioxide-reversibly-protected chain extension-crosslinking agent, wherein the aliphatic diamine is aliphatic alkane diamine, aliphatic ether diamine or aliphatic ester diamine, and the aliphatic triamine is aliphatic alkane triamine.

In an embodiment of the preparation method of the carbon dioxide-reversibly-protected chain extension-crosslinking agent of the present disclosure, aliphatic diamine or aliphatic triamine with 20 carbon atoms or fewer is dissolved in an organic solvent to obtain a mixture; the mixture is stirred and reacted at 0-35° C. under an atmosphere of carbon dioxide at a flow rate of 1-20 ml/min for 5-60 min; and after the completion of the reaction, the mixture is filtered, washed and dried to obtain the carbon dioxide-reversibly-protected chain extension-crosslinking agent. The molar ratio of the carbon dioxide to the aliphatic diamine or the aliphatic triamine is in a range of 1~2:1, and the molar ratio, for example, may be 1.5:1, 1.8:1, 2:1, and so on.

In an embodiment of the preparation method of carbon dioxide-reversibly-protected chain extension-crosslinking agent of the present disclosure, for polyamines with few carbon atom numbers (for example, diamines with less than 6 carbon atoms or triamines with less than 8 carbon atoms) that have high reactivities, a relatively small flow rate of carbon dioxide is selected to make sure carbon dioxide reacts with polyamine completely, and for polyamines with more carbon atoms, a larger flow rate of carbon dioxide may be selected to reduce the reaction time.

In an embodiment of the preparation method of carbon dioxide-reversibly-protected chain extension-crosslinking agent of the present disclosure, the organic solvent is not specifically limited, as long as it can dissolve the raw materials. Preferably, the organic solvent is tetrahydrofuran (THF).

The aliphatic diamine may be aliphatic alkane diamine, such as ethylenediamine, 1,6-hexanediamine, and 1,10-decanediamine; an aliphatic ether diamine, such as 2,2'-oxybis (ethylamine), 2,2'[1,2-ethylenedi(oxy)]bis-ethylamine, 2,2' [oxybis(2,1-ethyleneoxy)]bis-ethylamine, and 1-(2-aminoethoxy)propan-2-amine; or an aliphatic ester diamine, such as 1-amino-2-propyl carbamate. The aliphatic triamine may be aliphatic alkane triamine, such as N,N-bis(aminomethyl)- methanediamine, N,N-bis(2-aminoethyl)-1,2-ethylenediamine, and N,N-bis(4-aminobutyl)-1,4-butanediamine. Diethyl ether is typically used as washing agent to remove the tetrahydrofuran in the product.

In the technical solution mentioned above, the reaction temperatures and reaction times are preferably varied depending on different types of the aliphatic polyamines. When the aliphatic polyamine is aliphatic alkane diamine, preferably, the stirring speed is 100-300 rpm and the reaction time is 5-30 min. When the aliphatic polyamine is aliphatic ether diamine, aliphatic ester diamine, or aliphatic triamine, preferably, the stirring speed is 100-400 rpm, and the reaction time is 20-60 min. When the aliphatic polyamine is aliphatic triamine or aliphatic diamine with 6 carbon atoms or fewer, the reaction temperature is preferably 0-10° C., and the reaction temperature can be achieved by reacting in an ice-water bath.

The present disclosure also provides use of the carbon dioxide-reversibly-protected chain extension-crosslinking agent or the carbon dioxide-reversibly-protected chain extension-crosslinking agent prepared by the method of the present disclosure in the preparation of polyurethane material. The steps are typically as follows:

step I: adding an oligomeric polyol with a molecular weight of 1000-3000 to a reactor, dewatering it at 100-300° C. under a vacuum of 50-500 Pa, adding diisocyanate under the protection of an inert atmosphere, and heating the reaction mixture to 70-130° C., to obtain a polyurethane prepolymer with an NCO content of 3%-9% as desired;

step II: dispersing the carbon dioxide-reversibly-protected chain extension-crosslinking agent in an organic solvent to obtain a dispersion, adding the dispersion to the polyurethane prepolymer, stirring them at 100-300 rpm for 10-30 min to mix them evenly, and then removing the organic solvent to obtain a mixture, wherein removing the organic solvent may be performed by de-gassing the system with the help of a cold trap under a vacuum of 50-500 Pa for 5-30 min or heating the system at 80-100° C. for 2-3 h; and step III: reacting the mixture obtained in step II at 80-200° C. for 5-120 min, during which an active diamine is released from the chain extension-crosslinking agent and reacted with the polyurethane prepolymer, and then curing and molding the mixture to obtain a polyurethane elastomer.

In the technical solution mentioned above, the NCO content of the polyurethane prepolymer in step I may be determined by a di-n-butylamine method that is well known to those skilled in the art. In particular, m (about 0.5 g) of the prepolymer is weighed, and placed into a 250 ml Erlenmeyer flask; 25 ml of anhydrous toluene is added thereto; the Erlenmeyer flask is capped with a bottle plug, and shaken to completely dissolve the prepolymer; 20 ml of the solution of di-n-butylamine in anhydrous toluene is transferred into another Erlenmeyer flask with a pipet; the Erlenmeyer flask is capped with a bottle plug, and shaken for about 15 min; then 100 ml of isopropanol is added thereto, and 4-6 drops of indicator, bromocresol blue, is dropwise added thereto; the solution is titrated with a hydrochloric acid solution (concentration: $C_1$) until the color turns yellow from blue, and the volume of the hydrochloric acid consumed is recorded as $V_2$, while the hydrochloric acid consumed for a blank di-n-butylamine is recorded as $V_1$; and the NCO content is calculated according to the following equation:

$$NCO\% = (V_1 - V_2) * C_1 \times 4.2/m$$

In the technical solution mentioned above, the oligomeric polyol in step I is one or more selected from a polyester polyol, a polyether polyol, a polycarbonate polyol, and a polymeric polyol. The oligomeric polyol is preferably a poly(tetramethylene glycol) polyol (PTMG) with a polymerization degree n of 11-33; a poly(propylene oxide) polyol (PPO) with a polymerization degree m of 13-39; a polycarbonate polyol (PCDL) with a polymerization degree P of 4-17, wherein R is tetramethylene, pentamethylene, or hexamethylene; or a poly(ε-caprolactone) polyol (PCL) with a polymerization degree Q of 7-22. The structure formulae are shown as follows respectively:

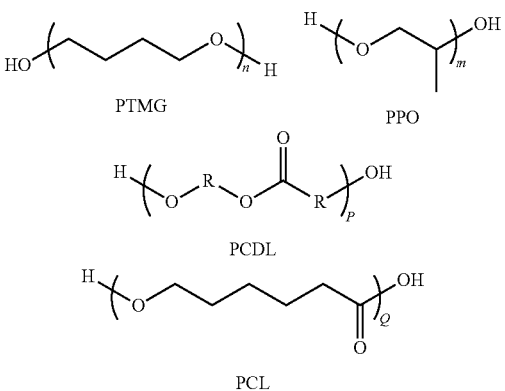

In the present disclosure, the above term "polymeric polyol" has the ordinary meaning in the art, and refers to a polyether polyol grafted with a vinyl polymer, abbreviated as a polyether polymeric polyol. The polymeric polyol is obtained by a radical grafting polymerization at a temperature of about 100° C. under a nitrogen atmosphere in which a vinyl monomer such as acrylonitrile, styrene, methyl methacrylate, vinyl acetate, and vinyl chloride and an initiator are added in a general polyether polyol as a base polyether (typically, a general soft foam polyether triol or highly active polyether).

In the technical solution mentioned above, the isocyanate in step I is one or more selected from toluene diisocyanate (TDI), diphenylmethane diisocyanate (MDI), 1,5-naphthalene diisocyanate (NDI), and p-phenylene diisocyanate (PPDI). The structure formulae are shown as follows respectively:

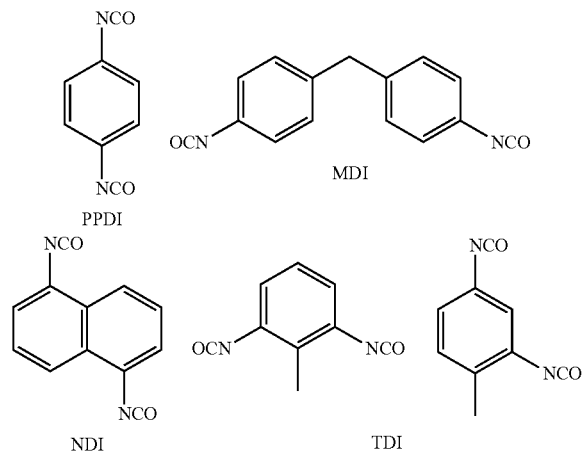

In the technical solution mentioned above, the organic solvent in step II has a dissolution function, and is not specifically limited. The organic solvent is preferably tetrahydrofuran (THF), N,N-dimethylformamide or acetone.

As compared to prior art, the present disclosure has the following advantageous effects.

In the carbon dioxide-reversibly-protected chain extension-crosslinking agents of the present disclosure, highly reactive aliphatic polyamines are protected reversibly by carbon dioxide to shield the activity of the aliphatic polyamines. As such, the highly active aliphatic polyamines can be mixed evenly with polyurethane prepolymers before gelation, and then transferred to a vulcanizer. The active aliphatic polyamines are released at an appropriate vulcanizing temperature and reacted with the prepolymer for curing and molding, resulting in final polyurethane material. In existing diamine-type chain extenders used in industry, large steric hindrance groups or electron-withdrawing groups are introduced into the diamine molecule, which permanently reduces the reactivity of the diamine. What's more the type and structure of diamines which can be used are not abundant. Therefore, as compared to prior art, the carbon dioxide-reversibly-protected chain extension-crosslinking agents of the present disclosure further extend applications of different forms of aliphatic polyamines as chain extension-crosslinking agents in synthesizing polyurethane material. Therefore, the carbon dioxide-reversibly-protected chain extension-crosslinking agents of the present disclosure have a wide range of potential applications in industry.

The preparation method of carbon dioxide-reversibly-protected chain extension-crosslinking agents and use of the carbon dioxide-reversibly-protected chain extension-crosslinking agents in the preparation of polyurethane material according to the present disclosure are both very simple and easy to operate.

The present disclosure will be further illustrated below with reference to the examples. The polyurethane starting materials used in the examples are commercially pure, and other reagents and chemicals are analytically pure. All of them are commercially available.

EXAMPLES

Example 1

The carbon dioxide-reversibly-protected chain extension-crosslinking agent has a structure as follows:

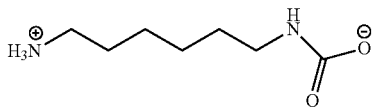 [SMILES: [NH3+]CCCCCCNC(=O)[O-]]

The preparation of the above carbon dioxide-reversibly-protected chain extension-crosslinking agent: 1,6-hexanediamine (5.81 g, 50 mmol) was dissolved in 500 ml tetrahydrofuran; carbon dioxide was introduced at a flow rate of 5 ml/min; the system was stirred at a rotation speed of 100 rpm for 0.5 h, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of PPO (molecular weight: 1000) was added to a three-necked flask, dewatered under a vacuum of 300 Pa at 130° C. for 2 h, and cooled to 70° C.; 16.9 g of MDI was added thereto under a nitrogen atmosphere, and then stirred for another 1.5 h to obtain a polyurethane prepolymer, wherein the NCO content of the polyurethane prepolymer was calculated as 5.6%;

step II: 5.35 g of the carbon dioxide-reversibly-protected chain extension-crosslinking agent was evenly dispersed in 20 ml tetrahydrofuran to obtain a dispersion; the dispersion was stirred at a speed of 300 rpm for 2 h, and transferred into the polyurethane prepolymer; the system was stirred at a rotation speed of 100 rpm at 70° C. for 2 h; tetrahydrofuran in the system was removed under a vacuum of 400 Pa for 1 h to obtain a mixture; and step III: the mixture obtained in step II was transferred into a vulcanizer in a period of 30 seconds, reacted in an opened mold at a vulcanization temperature of 150° C. for 10 min, and then cured and molded in the mold that was closed to obtain polyurethane elastomer.

The carbon dioxide-reversibly-protected chain extension-crosslinking agent of Example 1 was analyzed by nuclear magnetic resonance (NMR), and the data of the NMR spectrum (with deuterium oxide as deuterated reagent) were as follows: 164.77 ppm, 40.98 ppm, 39.25 ppm, 29.20 ppm, 26.86 ppm, 25.82 ppm, 5.08 ppm. It was confirmed that chain extension-crosslinking agent having a structure formula as shown above was obtained.

Example 2

The carbon dioxide-reversibly-protected chain extension-crosslinking agent has a structure as follows:

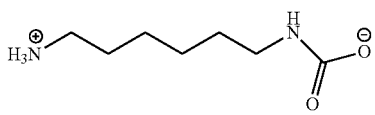 [SMILES: [NH3+]CCCCCCNC(=O)[O-]]

The preparation of the above carbon dioxide-reversibly-protected chain extension-crosslinking agent: 1,6-hexanediamine (5.81 g, 50 mmol) was dissolved in 500 ml tetrahydrofuran; carbon dioxide was introduced at a flow rate of 8 ml/min; the system was stirred at a rotation speed of 100 rpm for 0.5 h, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of PCDL (molecular weight: 2000) was added to a three-necked flask, heated to 130° C., dewatered at −0.98 MPa for 2 h, and cooled to 70° C.; 8.45 g of MDI was added thereto under a nitrogen atmosphere, and then stirred for another 1.5 h to obtain a polyurethane prepolymer, wherein the NCO content of the polyurethane prepolymer was determined as 3.36% by titration;

step II: 7 g of the carbon dioxide-reversibly-protected chain extension-crosslinking agent was evenly dispersed in 20 ml tetrahydrofuran to obtain a dispersion; the dispersion was stirred at a rotation speed of 100 rpm for 2 h, and transferred into the polyurethane prepolymer; the system was stirred at a rotation speed of 150 rpm at 70° C. for 2 h; tetrahydrofuran in the system was removed under a vacuum of 400 Pa for 1 h to obtain a mixture; and step III: the mixture in step II was transferred into a vulcanizer in a period of 30 seconds, reacted in an opened mold at a vulcanization temperature of 100° C. for 20 min, and then cured and molded in the mold that was closed to obtain a polyurethane.

The carbon dioxide-reversibly-protected chain extension-crosslinking agent of Example 2 was analyzed by NMR, and had the same result from NMR as that of Example 1.

Example 3

The carbon dioxide-reversibly-protected chain extension-crosslinking agent has a structure as follows:

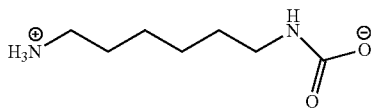 [SMILES: [NH3+]CCCCCCNC(=O)[O-]]

The preparation of the above carbon dioxide-reversibly-protected chain extension-crosslinking agent: 1,6-hexanediamine (5.81 g, 50 mmol) was dissolved in 500 ml tetrahydrofuran; carbon dioxide was introduced at a flow rate of 10 ml/min; the system was stirred at a rotation speed of 200 rpm for 0.5 h, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of PTMG (molecular weight: 1000) was added to a three-necked flask, heated to 130° C., dewatered at −0.98 MPa for 2 h, and cooled to 90° C.; 23.5 g of TDI80 was added thereto under a nitrogen atmosphere, and then stirred for another 4 h to obtain a polyurethane prepolymer, wherein the NCO content of the polyurethane prepolymer was determined as 9.89% by titration;

step II: 10.8 g of the carbon dioxide-reversibly-protected chain extension-crosslinking agent was evenly dispersed in 20 ml tetrahydrofuran; the dispersion was stirred at a rotation speed of 300 rpm for 2 h, and transferred into the polyurethane prepolymer; the system was stirred at a rotation speed of 300 rpm at 70° C. for 2 h; tetrahydrofuran in the system was removed under a vacuum of 450 Pa for 1 h to obtain a mixture; and step III: the mixture obtained in step II was transferred into a vulcanizer in a period of 30 seconds, reacted in an opened mold at a vulcanization temperature of 130° C. for 20 min, and then cured and molded in the mold that was closed to obtain a polyurethane.

The carbon dioxide-reversibly-protected chain extension-crosslinking agent of Example 3 was analyzed by NMR, and had the same result from NMR as that of Example 1.

Example 4

The carbon dioxide-reversibly-protected chain extension-crosslinking agent having a structure as follows:

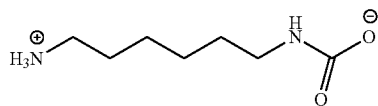 [SMILES: [NH3+]CCCCCCNC(=O)[O-]]

The preparation of the above carbon dioxide-reversibly-protected chain extension-crosslinking agent: 1,6-hexanediamine (5.81 g, 50 mmol) was dissolved in 500 ml tetrahydrofuran; carbon dioxide was introduced at a flow rate of 10 ml/min; the system was stirred at a rotation speed of 200 rpm for 0.5 h, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(ε-caprolactone) polyol (PCL, molecular weight: 2000) was added to a three-necked flask, heated to 130° C., dewatered under a vacuum of 400 Pa for 2 h, and cooled to 70° C.; 5.48 g of PPDI was added thereto under a nitrogen atmosphere, and then stirred for another 1.5 h to obtain a polyurethane prepolymer, wherein the NCO content of the polyurethane prepolymer was determined as 3.66% by titration;

step II: 7 g of the carbon dioxide-reversibly-protected chain extension-crosslinking agent was evenly dispersed in 20 ml tetrahydrofuran to obtain a dispersion; the dispersion was stirred at a rotation speed of 250 rpm for 2 h, and transferred into the polyurethane prepolymer; the system was stirred at a rotation speed of 250 rpm at 70° C. for 2 h; tetrahydrofuran in the system was removed under a vacuum of 200 Pa for 1 h to obtain a mixture; and step III: the mixture obtained in step II was transferred into a vulcanizer in a period of 30 seconds, reacted in an opened mold at a vulcanization temperature of 150° C. for 30 min, and then cured and molded in the mold that was closed to obtain a polyurethane.

The carbon dioxide-reversibly-protected chain extension-crosslinking agent of Example 4 was analyzed by NMR, and had the same result from NMR as that of Example 1.

Example 5

The carbon dioxide-reversibly-protected chain extension-crosslinking agent has a structure as follows:

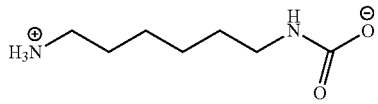 [SMILES: [NH3+]CCCCCCNC(=O)[O-]]

The preparation of the above carbon dioxide-reversibly-protected chain extension-crosslinking agent: 1,6-hexanediamine (5.81 g, 50 mmol) was dissolved in 500 ml tetrahydrofuran; carbon dioxide was introduced at a flow rate of 10 ml/min; the system was stirred at a rotation speed of 200 rpm for 0.5 h, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(propylene oxide) polyol (PPG, molecular weight: 2000) was added to a three-necked flask, heated to 130° C., dewatered under a vacuum of 400 Pa for 2 h, and cooled to 70° C.; 8.45 g of MDI was added thereto under a nitrogen atmosphere, and then stirred for another 1.5 h to obtain a polyurethane prepolymer, wherein the NCO content of the polyurethane prepolymer was determined as 3.36% by titration;

step II: 2.71 g of the carbon dioxide-reversibly-protected chain extension-crosslinking agent was evenly dispersed in 20 ml tetrahydrofuran to obtain a dispersion; the dispersion was stirred at a rotation speed of 250 rpm for 2 h, and transferred into the polyurethane prepolymer; the system was stirred at a rotation speed of 250 rpm at 70° C. for 2 h; tetrahydrofuran in the system was removed under a vacuum of 200 Pa for 1 h to obtain a mixture; and step III: the mixture obtained in step II was transferred into a vulcanizer in a period of 30 seconds, reacted in an opened mold at a vulcanization temperature of 150° C. for 30 min, and then cured and molded in the mold that was closed to obtain a polyurethane.

The carbon dioxide-reversibly-protected chain extension-crosslinking agent of Example 5 was analyzed by NMR, and had the same result from NMR as that of Example 1.

Example 6

The carbon dioxide-reversibly-protected chain extension-crosslinking agent has a structure as follows:

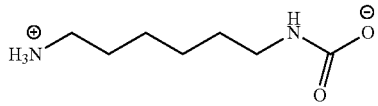 [SMILES: [NH3+]CCCCCCNC(=O)[O-]]

The preparation of the above carbon dioxide-reversibly-protected chain extension-crosslinking agent: 1,6-hexanediamine (5.81 g, 50 mmol) was dissolved in 500 ml tetrahydrofuran; carbon dioxide was introduced at a flow rate of 10 ml/min; the system was stirred at a rotation speed of 200 rpm for 0.5 h, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 20 g of PPG (molecular weight: 2000) was added to a three-necked flask, heated to 130° C., dewatered under a vacuum of 400 Pa for 2 h, and cooled to 70° C.; 4.45 g of IPDI was added thereto under a nitrogen atmosphere, and then stirred for another for 1.5 h to obtain a polyurethane prepolymer, wherein the NCO content of the polyurethane prepolymer was determined as 3.43% by titration;

step II: 1.6 g of the carbon dioxide-reversibly-protected chain extension-crosslinking agent was evenly dispersed in 20 ml tetrahydrofuran to obtain a dispersion; the dispersion was stirred at a rotation speed of 250 rpm for 2 h, and transferred into the polyurethane prepolymer; the system was stirred at a rotation speed of 250 rpm at 70° C. for 2 h; tetrahydrofuran in the system was removed under a vacuum of 200 Pa for 1 h to obtain a mixture; and step III: the mixture obtained in step II was transferred into a vulcanizer in a period of 30 seconds, reacted in an opened mold at a vulcanization temperature of 150° C. for 30 min, and then cured and molded in the mold that was closed to obtain a polyurethane.

The carbon dioxide-reversibly-protected chain extension-crosslinking agent of Example 6 was analyzed by NMR, and had the same result from NMR as that of Example 1.

Example 7

The carbon dioxide-reversibly-protected chain extension-crosslinking agent has a structure as follows:

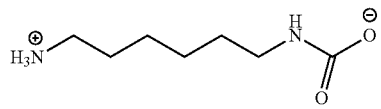 [SMILES: [NH3+]CCCCCCNC(=O)[O-]]

The preparation of the above carbon dioxide-reversibly-protected chain extension-crosslinking agent: 1,6-hexanediamine (5.81 g, 50 mmol) was dissolved in 500 ml tetrahydrofuran; carbon dioxide was introduced at a flow rate of 10 ml/min; the system was stirred at a rotation speed of 200 rpm for 0.5 h, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 20 g of poly(propylene oxide) polyol (PPG, molecular weight: 1000) was added to a three-necked flask, heated to 130° C., dewatered under a vacuum of 400 Pa for 2 h, and cooled to 70° C.; 8.89 g of IPDI was added thereto under a nitrogen atmosphere, and stirred for another 1.5 h to obtain a polyurethane prepolymer, wherein the NCO content of the polyurethane prepolymer was determined as 5.62% by titration;

step II: 3.09 g of the carbon dioxide-reversibly-protected chain extension-crosslinking agent was evenly dispersed in 20 ml tetrahydrofuran to obtain a dispersion; the dispersion was stirred at a rotation speed of 250 rpm for 2 h, and transferred into the polyurethane prepolymer; the system was stirred at a rotation speed of 250 rpm at 70° C. for 2 h; tetrahydrofuran in the system was removed under a vacuum of 200 Pa for 1 h to obtain a mixture; and step III: the mixture obtained in step II was transferred into a vulcanizer in a period of 30 seconds, reacted in an opened mold at a vulcanization temperature of 150° C. for 30 min, and then cured and molded in the mold that was closed to obtain a polyurethane.

The carbon dioxide-reversibly-protected chain extension-crosslinking agent of Example 7 was analyzed by NMR, and had the same result from NMR as that of Example 1.

Example 8

The carbon dioxide-reversibly-protected chain extension-crosslinking agent has a structure as follows:

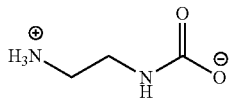

The preparation of the above carbon dioxide-reversibly-protected chain extension-crosslinking agent: ethylenediamine (2 g, 33 mmol) was dissolved in 500 ml tetrahydrofuran; under a temperature of 5° C., carbon dioxide was introduced at a flow rate of 3 ml/min; the system was stirred at a rotation speed of 200 rpm for 40 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(c-caprolactone) polyol (PCL, molecular weight: 2000) was added to a three-necked flask, heated to 130° C., dewatered under a vacuum of 300 Pa for 2 h, and cooled to 70° C.; 5.48 g of PPDI was added thereto under a nitrogen atmosphere, and then stirred for another 1.5 h to obtain a polyurethane prepolymer, wherein the NCO content of the polyurethane prepolymer was determined as 3.66% by titration;

step II: 1.03 g of the carbon dioxide-reversibly-protected chain extension-crosslinking agent was evenly dispersed in 20 ml tetrahydrofuran to obtain a dispersion; the dispersion was stirred at a rotation speed of 250 rpm for 2 h, and transferred into the polyurethane prepolymer; the system was stirred at a rotation speed of 250 rpm at 70° C. for 2 h; tetrahydrofuran in the system was removed under a vacuum of 300 Pa for 1 h to obtain a mixture; and step III: the mixture obtained in step II was transferred into a vulcanizer in a period of 30 seconds, reacted in an opened mold at a vulcanization temperature of 150° C. for 30 min, and then cured and molded in the mold that was closed to obtain a polyurethane.

The carbon dioxide-reversibly-protected chain extension-crosslinking agent of Example 5 was analyzed by nuclear magnetic resonance (NMR), and the data of the NMR spectrum (with deuterium oxide as deuterated reagent) were as follows: 166.98 ppm, 42.71 ppm, 41.2 ppm. It was confirmed that the chain extension-crosslinking agent has a structure formula as shown above was prepared in Example 8.

Example 9

The carbon dioxide-reversibly-protected chain extension-crosslinking agent has a structure as follows:

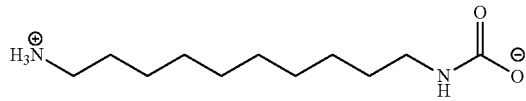 [SMILES: [NH3+]CCCCCCCCCCNC(=O)[O-]]

The preparation of the above carbon dioxide-reversibly-protected chain extension-crosslinking agent: 1,10-decanediamine (2 g, 9.2 mmol) was dissolved in 500 ml tetrahydrofuran; carbon dioxide was introduced at a flow rate of 20 ml/min; the system was stirred at a rotation speed of 200 rpm for 40 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(ε-caprolactone) polyol (PCL, molecular weight: 2000) was added to a three-necked flask, heated to 130° C., dewatered under a vacuum of 300 Pa for 2 h, and cooled to 70° C.; 5.48 g of PPDI was added thereto under a nitrogen atmosphere, and then stirred for another 1.5 h to obtain a polyurethane prepolymer, wherein the NCO content of the polyurethane prepolymer was determined as 3.66% by titration;

step II: 2.06 g of the carbon dioxide-reversibly-protected chain extension-crosslinking agent was evenly dispersed in 20 ml tetrahydrofuran to obtain a dispersion; the dispersion was stirred at a rotation speed of 250 rpm for 2 h, and transferred into the polyurethane prepolymer; the system was stirred at a rotation speed of 250 rpm at 70° C. for 2 h; tetrahydrofuran in the system was removed under a vacuum of 300 Pa for 1 h to obtain a mixture; and step III: the mixture obtained in step II was transferred into a vulcanizer in a period of 30 seconds, reacted in an opened mold at a vulcanization temperature of 150° C. for 30 min, and then cured and molded in the mold that was closed to obtain a polyurethane.

The carbon dioxide-reversibly-protected chain extension-crosslinking agent of Example 9 was analyzed by nuclear magnetic resonance (NMR), and the data of the NMR spectrum (with deuterium oxide as deuterated reagent) were as follows: 163.24 ppm, 42.5 ppm, 40.2 ppm, 32.5 ppm, 30.9 ppm, 29.3 ppm, 26.7 ppm, 25.5 ppm. It was confirmed that the chain extension-crosslinking agent having a structure formula as shown above was prepared in Example 9.

Example 10

The carbon dioxide-reversibly-protected chain extension-crosslinking agent has a structure as follows:

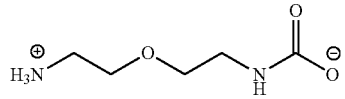

The preparation of the above carbon dioxide-reversibly-protected chain extension-crosslinking agent: 2,2'-oxybis(ethylamine) (2 g, 19.2 mmol) was dissolved in 500 ml tetrahydrofuran; carbon dioxide was introduced at a flow rate of 13 ml/min; the system was stirred at a rotation speed of 200 rpm for 25 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(tetramethylene glycol) polyol (PTMG, molecular weight: 2000) was added to a three-necked flask, heated to 130° C., dewatered under a vacuum of 300 Pa for 2 h, and cooled to 70° C.; 7.1 g of NDI was added thereto under a nitrogen atmosphere, and then stirred for another 1.5 h to obtain a polyurethane prepolymer, wherein the NCO content of the polyurethane prepolymer was determined as 3.47% by titration;

step II: 1.52 g of the carbon dioxide-reversibly-protected chain extension-crosslinking agent was evenly dispersed in 20 ml tetrahydrofuran to obtain a dispersion; the dispersion was stirred at a rotation speed of 250 rpm for 2 h, and transferred into 20 g of the polyurethane prepolymer obtained in step I; the system was stirred at a rotation speed of 300 rpm at 70° C. for 1 h; tetrahydrofuran in the system was removed under a vacuum of 300 Pa for 1 h to obtain a mixture; and step III: the mixture obtained in step II was transferred into a vulcanizer in a period of 30 seconds, reacted in an opened mold at a vulcanization temperature of 100° C. for 10 min, and then cured and molded in the mold that was closed to obtain a polyurethane.

The carbon dioxide-reversibly-protected chain extension-crosslinking agent of Example 10 was analyzed by nuclear magnetic resonance (NMR), and the data of the NMR spectrum (with deuterium oxide as deuterated reagent) were as follows: 163.84 ppm, 74.4 ppm, 69.8 ppm, 42.6 ppm, 41.5 ppm. It was confirmed that the chain extension-crosslinking agent having a structure formula as shown above was prepared in Example 10.

Example 11

The carbon dioxide-reversibly-protected chain extension-crosslinking agent has a structure as follows:

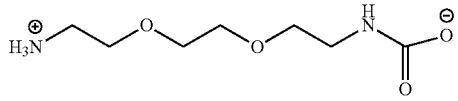 [SMILES: [NH3+]CCOCCOCCNC(=O)[O-]]

The preparation of the above carbon dioxide-reversibly-protected chain extension-crosslinking agent: 2,2'[1,2-ethylenedi(oxy)]bis-ethylamine (3 g, 20.3 mmol) was dissolved in 500 ml tetrahydrofuran; carbon dioxide was introduced at a flow rate of 10 ml/min; the system was stirred at a rotation speed of 200 rpm for 40 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(ε-caprolactone) polyol (PCL, molecular weight: 2000) was added to a three-necked flask, heated to 130° C., dewatered under a vacuum of 300 Pa for 2 h, and cooled to 70° C.; 7.1 g of NDI was added thereto under a nitrogen atmosphere, and then stirred for another 1.5 h to obtain a polyurethane prepolymer, wherein the NCO content of the polyurethane prepolymer was determined as 3.47% by titration;

step II: 1.7 g of the carbon dioxide-reversibly-protected chain extension-crosslinking agents were evenly dispersed in 20 ml tetrahydrofuran to obtain a dispersion; the dispersion was stirred at a rotation speed of 250 rpm for 2 h, and transferred into 22 g of the polyurethane prepolymer obtained in step I; the system was stirred at a rotation speed of 300 rpm at 70° C. for 1 h; tetrahydrofuran in the system was removed under a vacuum of 400 Pa for 1 h to obtain a mixture; and step III: the mixture obtained in step II was transferred into a vulcanizer in a period of 30 seconds, reacted in an opened mold at a vulcanization temperature of 130° C. for 15 min, and then cured and molded in the mold that was closed to obtain a polyurethane.

The carbon dioxide-reversibly-protected chain extension-crosslinking agent of Example 11 was analyzed by nuclear magnetic resonance (NMR), and the data of the NMR spectrum (with deuterium oxide as deuterated reagent) were as follows: 163.59 ppm, 74.7 ppm, 70.8 ppm, 70.3 ppm, 70.1 ppm, 42.6 ppm, 41.5 ppm. It was confirmed that the chain extension-crosslinking agent having a structure formula as shown above was prepared in Example 11.

Example 12

The carbon dioxide-reversibly-protected chain extension-crosslinking agent has a structure as follows:

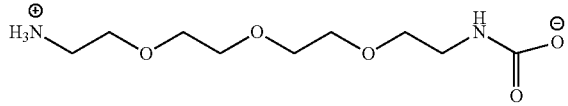 [SMILES: [NH3+]CCOCCOCCOCCNC(=O)[O-]]

The preparation of the above carbon dioxide-reversibly-protected chain extension-crosslinking agent: 2,2'[oxybis(2,1-ethyleneoxy)]bis-ethylamine (2 g, 10.4 mmol) was dissolved in 500 ml tetrahydrofuran; carbon dioxide was introduced at a flow rate of 10 ml/min; the system was stirred at a rotation speed of 200 rpm for 50 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(propylene oxide) polyol (PPO, molecular weight: 2000) was added to a three-necked flask, heated to 130° C., dewatered under a vacuum of 300 Pa for 2 h, and cooled to 70° C.; 8.45 g of MDI was added thereto under a nitrogen atmosphere, and then stirred for another 1.5 h to obtain a polyurethane prepolymer, wherein the NCO content of the polyurethane prepolymer was determined as 3.34% by titration;

step II: 1.87 g of the carbon dioxide-reversibly-protected chain extension-crosslinking agent was evenly dispersed in 20 ml tetrahydrofuran to obtain a dispersion; the dispersion was stirred at a rotation speed of 300 rpm for 2 h, and transferred into 20 g of the polyurethane prepolymer obtained in step I; the system was stirred at a rotation speed of 300 rpm at 70° C. for 1 h; tetrahydrofuran in the system was removed under a vacuum of 400 Pa for 1 h to obtain a mixture; and step III: the mixture obtained in step II was transferred into a vulcanizer in a period of 30 seconds, reacted in an opened mold at a vulcanization temperature of 130° C. for 20 min, and then cured and molded in the mold that was closed to obtain a polyurethane.

The carbon dioxide-reversibly-protected chain extension-crosslinking agent of Example 12 was analyzed by nuclear magnetic resonance (NMR), and the data of the NMR spectrum (with deuterium oxide as deuterated reagent) were as follows: 163.37 ppm, 74.3 ppm, 71.9 ppm, 70.5 ppm, 70.1 ppm, 69.6 ppm, 69.2 ppm, 43.6 ppm, 41.5 ppm. It was confirmed that the chain extension-crosslinking agent having a structure formula as shown above was prepared in Example 12.

Example 13

The carbon dioxide-reversibly-protected chain extension-crosslinking agent have a structure as follows:

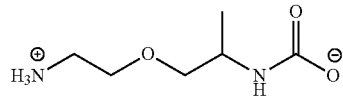

The preparation of the above carbon dioxide-reversibly-protected chain extension-crosslinking agent: 1-am ino-2-propyl carbamate (2 g, 18.5 mmol) was dissolved in 500 ml tetrahydrofuran; carbon dioxide was introduced at a flow rate of 15 ml/min; the system was stirred at a rotation speed of 300 rpm for 40 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(propylene oxide) polyol (PPO, molecular weight: 2000) was added to a three-necked flask, heated to 130° C., dewatered under a vacuum of 300 Pa for 2 h, and cooled to 70° C.; 8.45 g of MDI was added thereto under a nitrogen atmosphere, and then stirred for another 1.5 h to obtain a polyurethane prepolymer, wherein the NCO content of the polyurethane prepolymer was determined as 3.34% by titration;

step II: 1.28 g of the carbon dioxide-reversibly-protected chain extension-crosslinking agent was evenly dispersed in 20 ml tetrahydrofuran to obtain a dispersion; the dispersion was stirred at a rotation speed of 300 rpm for 2 h, and transferred into 20 g of the polyurethane prepolymer obtained in step I; the system was stirred at a rotation speed of 300 rpm at 70° C. for 1 h; tetrahydrofuran in the system was removed under a vacuum of 400 Pa for 1 h to obtain a mixture; and step III: the mixture obtained in step II was transferred into a vulcanizer in period of 30 seconds, reacted in an opened mold at a vulcanization temperature of 100° C. for 60 min, and then cured and molded in the mold that was closed to obtain a polyurethane.

The carbon dioxide-reversibly-protected chain extension-crosslinking agent of Example 13 was analyzed by nuclear magnetic resonance (NMR), and the data of the NMR spectrum (with deuterium oxide as deuterated reagent) were as follows: 163 ppm, 78.1 ppm, 74.9 ppm, 49.6 ppm, 41.5 ppm, 17.3 ppm. It was confirmed that the chain extension-crosslinking agent having a structure formula as shown above was prepared in Example 13.

Example 14

The carbon dioxide-reversibly-protected chain extension-crosslinking agent has a structure as follows:

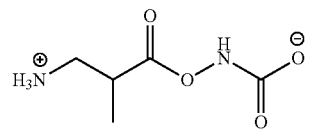

The preparation of the above carbon dioxide-reversibly-protected chain extension-crosslinking agent: 1-am ino-2-propyl carbamate (2 g, 16.9 mmol) was dissolved in 500 ml tetrahydrofuran; carbon dioxide was introduced at a flow rate of 10 ml/min; the system was stirred at a rotation speed of 300 rpm for 30 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of polycarbonate polyol (PCDL, molecular weight: 2000) was added to a three-necked flask, heated to 130° C., dewatered under a vacuum of 300 Pa for 2 h, and cooled to 70° C.; 8.45 g of MDI was added thereto under a nitrogen atmosphere, and then stirred for another 1.5 h to obtain a polyurethane prepolymer, wherein the NCO content of the polyurethane prepolymer was determined as 3.34% by titration;

step II: 1.28 g of the carbon dioxide-reversibly-protected chain extension-crosslinking agent was evenly dispersed in 20 ml tetrahydrofuran to obtain a dispersion; the dispersion was stirred at a rotation speed of 300 rpm for 2 h, and transferred into 20 g of the polyurethane prepolymer obtained in step I; the system was stirred at a rotation speed of 300 rpm at 70° C. for 1 h; tetrahydrofuran in the system was removed under a vacuum of 400 Pa for 1 h to obtain a mixture; and step III: the mixture obtained in step II was transferred into a vulcanizer in a period of 30 seconds, reacted in an opened mold at a vulcanization temperature of 100° C. for 20 min, and then cured and molded in the mold that was closed to obtain a polyurethane.

The carbon dioxide-reversibly-protected chain extension-crosslinking agent of Example 14 was analyzed by nuclear magnetic resonance (NMR), and the data of the NMR spectrum (with deuterium oxide as deuterated reagent) were as follows: 178.9 ppm, 158 ppm, 41.7 ppm, 36.4 ppm, 14.2 ppm. It was confirmed that the chain extension-crosslinking agent having a structure formula as shown above was prepared in Example 14.

Example 15

The carbon dioxide-reversibly-protected chain extension-crosslinking agent has a structure as follows:

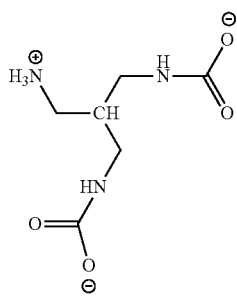 [SMILES: [NH3+]CC(CNC(=O)[O-])CNC(=O)[O-]]

The preparation of the above carbon dioxide-reversibly-protected chain extension-crosslinking agent: N,N-bis(aminomethyl)-methanediamine (2 g, 16.9 mmol) was dissolved in 500 ml tetrahydrofuran; at a temperature of 0° C., carbon dioxide was introduced at a flow rate of 5 ml/min; the system was stirred at a rotation speed of 300 rpm for 40 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(tetramethylene glycol) polyol (PTMG, molecular weight: 2000) was added to a three-necked flask, heated to 130° C., dewatered under a vacuum of 300 Pa for 2 h, and cooled to 70° C.; 8.45 g of MDI was added thereto under a nitrogen atmosphere, and then stirred for another 1.5 h to obtain a polyurethane prepolymer, wherein the NCO content of the polyurethane prepolymer was determined as 3.34% by titration;

step II: 1.35 g of the carbon dioxide-reversibly-protected chain extension-crosslinking agent was evenly dispersed in 20 ml tetrahydrofuran; the dispersion was stirred at a rotation speed of 300 rpm for 2 h, and transferred into 20 g of the polyurethane prepolymer obtained in step I; the system was stirred at a rotation speed of 300 rpm at 60° C. for 1 h; tetrahydrofuran in the system was removed under a vacuum of 400 Pa for 1 h to obtain a mixture; and step III: the mixture obtained in step II was transferred into a vulcanizer in a period of 30 seconds, reacted in an opened mold at a vulcanization temperature of 80° C. for 10 min, and then cured and molded in the mold that was closed to obtain a polyurethane.

The carbon dioxide-reversibly-protected chain extension-crosslinking agent of Example 15 was analyzed by nuclear magnetic resonance (NMR), and the data of the NMR spectrum (with deuterium oxide as deuterated reagent) were as follows: 164 ppm, 40.5 ppm, 38.9 ppm, 38.1 ppm. It was confirmed that the chain extension-crosslinking agent having a structure formula as shown above was prepared in Example 15.

Example 16

The carbon dioxide-reversibly-protected chain extension-crosslinking agent has a structure as follows:

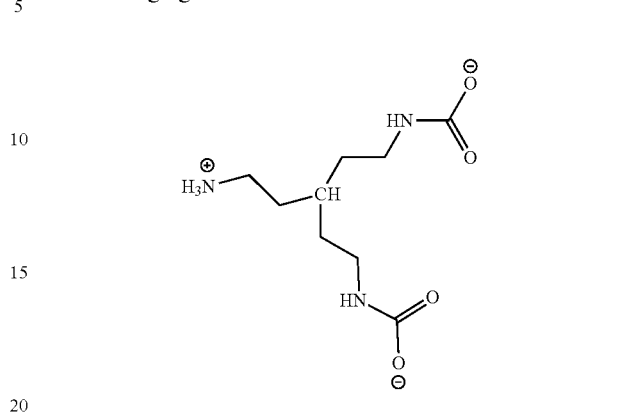

The preparation of the above carbon dioxide-reversibly-protected chain extension-crosslinking agent: N,N-bis(2-aminoethyl)-1,2-ethylenediamine (2 g, 13.7 mmol) was dissolved in 500 ml tetrahydrofuran; at 5° C., carbon dioxide was introduced at a flow rate of 10 ml/min; the system was stirred at a rotation speed of 300 rpm for 40 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(tetramethylene glycol) polyol (PTMG, molecular weight: 2000) was added to a three-necked flask, heated to 130° C., dewatered under a vacuum of 300 Pa for 2 h, and cooled to 70° C.; 5.4 g of PPDI was added thereto under a nitrogen atmosphere, and then stirred for another 1.5 h to obtain a polyurethane prepolymer, wherein the NCO content of the polyurethane prepolymer was determined as 3.6% by titration;

step II: 1.99 g of the carbon dioxide-reversibly-protected chain extension-crosslinking agent was evenly dispersed in 20 ml tetrahydrofuran to obtain a dispersion; the dispersion was stirred at a rotation speed of 300 rpm for 2 h, and transferred into 20 g of the polyurethane prepolymer obtained in step I; the system was stirred at a rotation speed of 300 rpm at 60° C. for 1 h; tetrahydrofuran in the system was removed under a vacuum of 300 Pa for 1 h to obtain a mixture; and step III: the mixture obtained in step II was transferred into a vulcanizer in a period of 30 seconds, reacted in an opened mold at a vulcanization temperature of 100° C. for 15 min, and then cured and molded in the mold that was closed to obtain a polyurethane.

The carbon dioxide-reversibly-protected chain extension-crosslinking agent of Example 16 was analyzed by nuclear magnetic resonance (NMR), and the data of the NMR spectrum (with deuterium oxide as deuterated reagent) were as follows: 163 ppm, 56.4 ppm, 53.6 ppm, 40.7 ppm, 39.6 ppm, 38.1 ppm. It was confirmed that the chain extension-crosslinking agent having a structure formula as shown above was prepared in Example 16.

Example 17

The carbon dioxide-reversibly-protected chain extension-crosslinking agent have a structure as follows:

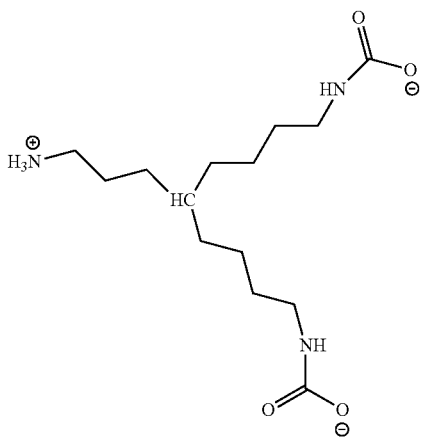 [SMILES: [NH3+]CCCC(CCCCNC(=O)[O-])CCCCNC(=O)[O-]]

The preparation of the above carbon dioxide-reversibly-protected chain extension-crosslinking agent: N,N-bis(4-aminobutyl)-1,4-butanediamine (3 g, 13 mmol) was dissolved in 500 ml tetrahydrofuran; at 10° C., carbon dioxide was introduced at a flow rate of 20 ml/min; the system was stirred at a rotation speed of 300 rpm for 40 min, filtered, washed with diethyl ether, and dried to obtain the carbon dioxide-reversibly-protected chain extension-crosslinking agent.

Use of the carbon dioxide-reversibly-protected chain extension-crosslinking agent mentioned above in the preparation of polyurethane elastomer:

step I: 33.8 g of poly(ε-caprolactone) polyol (PCL, molecular weight: 2000) was added to a three-necked flask, heated to 130° C., dewatered under a vacuum of 300 Pa for 2 h, and cooled to 70° C.; 5.4 g of PPDI was added thereto under a nitrogen atmosphere, and then stirred for another 1.5 h to obtain a polyurethane prepolymer, wherein the NCO content of the polyurethane prepolymer was determined as 3.6% by titration;

step II: 2.71 g of the carbon dioxide-reversibly-protected chain extension-crosslinking agent was evenly dispersed in 20 ml tetrahydrofuran; the dispersion was stirred at a rotation speed of 300 rpm for 2 h, and transferred into 20 g of the polyurethane prepolymer obtained in step I; the system was stirred at a rotation speed of 300 rpm at 60° C. for 1 h; tetrahydrofuran in the system was removed under a vacuum of 300 Pa for 1 h to obtain a mixture; and step III: the mixture obtained in step II was transferred into a vulcanizer in a period of 30 seconds, reacted in an opened mold at a vulcanization temperature of 100° C. for 15 min, and then cured and molded in the mold that was closed to obtain a polyurethane.

The carbon dioxide-reversibly-protected chain extension-crosslinking agent of Example 17 was analyzed by nuclear magnetic resonance (NMR), and the data of the NMR spectrum (with deuterium oxide as deuterated reagent) were as follows: 163 ppm, 56.9 ppm, 42.2 ppm, 39.9 ppm, 38.1 ppm, 27.6 ppm, 25.9 ppm, 24.4 ppm. It was confirmed that the chain extension-crosslinking agent having a structure formula as shown above was prepared in Example 17.

Comparative Example 1

The preparation of polyurethane elastomer with diol as a chain extender:
step I: the prepolymer was prepared in the same manner as in Example 1; and
step II: 2.02 g of 1,6-hexanediol was added to the polyurethane prepolymer; the mixture was sufficiently mixed under stirring, and transferred to a vulcanizer at 130° C. to obtain a polyurethane elastomer that was chain-extended with diol.

Comparative Example 2

The preparation of polyurethane elastomer with diol as a chain extender:
step I: preparing the prepolymer in the same manner as in Example 2; and
step II: 2 g of 1,6-hexanediol was added to the polyurethane prepolymer; the mixture was sufficiently mixed under stirring, and transferred to a vulcanizer at 130° C. to obtain a polyurethane elastomer that was chain-extended with diol.

Comparative Example 3

The preparation of polyurethane elastomer with diol as a chain extender:
step I: the prepolymer was prepared in the same manner as in Example 3; and
step II: 7.97 g of 1,6-hexanediol was added to the polyurethane prepolymer; the mixture was sufficiently mixed under stirring, and transferred to a vulcanizer at 130° C. to obtain a polyurethane elastomer that was chain-extended with diol.

Comparative Example 4

The preparation of polyurethane elastomer with diol as a chain extender:
step I: the prepolymer was prepared in the same manner as in Example 4; and
step II: 2.02 g of 1,6-hexanediol was added to the polyurethane prepolymer; the mixture was sufficiently mixed under stirring, and transferred to a vulcanizer at 130° C. to obtain a polyurethane elastomer that was chain-extended with diol.

Comparative Example 5

The preparation of polyurethane elastomer with diol as a chain extender:
step I: the prepolymer was prepared in the same manner as in Example 5; and
step II: 2 g of 1,6-hexanediol was added to the polyurethane prepolymer; the mixture was sufficiently mixed under stirring, and transferred to a vulcanizer at 130° C. to obtain a polyurethane elastomer chain-extended with diol.

Comparative Example 6

The preparation of polyurethane elastomer with diol as a chain extender:
step I: the prepolymer was prepared in the same manner as in Example 6; and
step II: 1.18 g of 1,6-hexanediol was added to the polyurethane prepolymer; the mixture was sufficiently mixed under stirring, and transferred to a vulcanizer at 130° C. to obtain a polyurethane elastomer chain-extended with diol.

Comparative Example 7

The preparation of polyurethane elastomers with diol as a chain extender:
step I: the prepolymer was prepared in the same manner as in Example 7; and
step II: 2.28 g of 1,6-hexanediol was added to the polyurethane prepolymer; the mixture was sufficiently mixed under stirring, and transferred to a vulcanizer at 130° C. to obtain a polyurethane elastomer chain-extended with diol.

Mechanical properties were tested for the polyurethane elastomers of Examples 1-17 and Comparative Examples 1-7. The testing method was as follows: (1) the polyurethane elastomer was cut into 5 same specimens according to the size of #4 dumbbell specimen specified in National Standard GB/T528-2009, and a length, a width and a thickness of each specimen were measured before stretching measurement; and (2) the stretching was applied with an INSTRON5982 type electronic tensile testing machine at a stretching rate of 200 mm/min with a preloaded force of 2 N; after stretching, the elasticity modulus, elongation at break and tensile strength of each specimen were calculated. The testing results are shown in table 1, table 2 and table 3.

TABLE 1

Test results for the mechanical properties of the polyurethane elastomers of Examples 1-4 and Comparative Examples 1-4

| Items | Example 1 | Comparative Example 1 | Example 2 | Comparative Example 2 | Example 3 | Comparative Example 3 | Example 4 | Comparative Example 4 |
|---|---|---|---|---|---|---|---|---|
| Elasticity modulus (MPa) | 65 | 4 | 18.4 | 6.9 | 105.2 | 10.6 | 30.6 | 17.0 |
| Tensile strength (MPa) | 19.2 | 16.6 | 3.4 | 7.1 | 12.4 | 18.1 | 15.6 | 32.6 |
| Elongation at break % | 366 | 1026 | 228 | 750 | 27.39 | 699 | 418.3 | 1139 |

TABLE 2

Test results for the mechanical properties of the polyurethane elastomers of Examples 5-7 and Comparative Examples 5-7

| Items | Example 5 | Comparative Example 5 | Example 6 | $^a$Comparative Example 6 | Example 7 | $^a$Comparative Example 7 |
|---|---|---|---|---|---|---|
| Elasticity modulus (MPa) | 1.6 | 19.1 | 3 | — | 7.8 | — |
| Tensile strength (MPa) | 6.9 | 9.7 | 10.1 | — | 13.4 | — |
| Elongation at break % | 2189 | 843 | 2561 | — | 1346 | — |

$^a$The phase separation of the system is too poor to obtain polyurethane elastomer, and thus its tensile properties cannot be characterized.

As can be seen from table 1 and table 2, when an unprotected diamine is directly mixed with the prepolymer, the gelation rate is too fast because of very vigorous reaction, and thus firstly chain-extended polyurethane encloses unreacted prepolymer, so that the unreacted prepolymer cannot be mixed evenly with the subsequently added diamine for chain-extension. Finally when the mixture is transferred into the vulcanizer for hot press molding, such unreacted prepolymer contained in the previously chain-extended polyurethane, which is not chain-extended, is extruded, and thus the whole polyurethane film has nearly no strength. When protected diamines are used as chain extenders, as compared to the prepolymer chain-extended with 1,6-hexanediol, the polyurethane chain-extended with diamine achieved higher tensile strength and elasticity modulus because of the introduction of more hydrogen bonding, but the elongation at break thereof decreases to some extent.

TABLE 3

Test results for the mechanical properties of the polyurethane elastomers of Examples 8-17

| Items | Example 8 | Example 9 | Example 10 | Example 11 | Example 12 | Example 13 | Example 14 | Example 15 | Example 16 | Example 17 |
|---|---|---|---|---|---|---|---|---|---|---|
| Elasticity modulus (MPa) | 10.1 | 18.9 | 12.4 | 24.1 | 30.5 | 38.6 | 27.9 | 43.9 | 27.5 | 16.2 |
| Tensile strength (MPa) | 20.7 | 16.5 | 19.3 | 18.7 | 24.3 | 24.3 | 26.4 | 24.3 | 16.3 | 28.1 |
| Elongation at break % | 439.3 | 229 | 300.4 | 425.5 | 626.3 | 170.8 | 270.6 | 130.7 | 226.3 | 346.0 |

As can be seen from table 3, through protection with carbon dioxide and deprotection, the polyurethane elastomers chain extended with aliphatic ether diamines, ester-based diamines or aliphatic triamines also achieve very good mechanical properties.

As can be seen from Examples 1-17, the method for reversibly protecting polyamine with carbon dioxide of the present disclosure can enable the preparation of polyurethane elastomer using polyamine with low molecular weight as a chain extender in conventional preparation system of polyurethane, and the obtained polyurethane elastomer has excellent mechanical properties.

Obviously, the above description of Examples is only intended to help understand the method and concept of the present disclosure. It should be noted that some modifications and variations can be made to the present disclosure by a person skilled in the art without departing from the method and principle of the present disclosure. These modifications and variations also fall within the protection scope of the claims of the present disclosure.

What is claimed is:

1. A carbon dioxide-reversibly-protected chain extension-crosslinking agent having a chemical structure represented by Formula II:

Formula II wherein m is an integer, R is either $OCH_2CH(CH_3)$ or $OCH_2CH_2$, and $1 \leq m \leq 10$.

2. The carbon dioxide-reversibly-protected chain extension-crosslinking agent according to claim 1, wherein $1 \leq m \leq 5$.

3. The carbon dioxide-reversibly-protected chain extension-crosslinking agent according to claim 1, wherein $1 \leq m \leq 3$.

4. A preparation method of a carbon dioxide-reversibly-protected chain extension-crosslinking agent according to claim 1, the method comprising:
dissolving aliphatic diamine with 20 carbon atoms or fewer in an organic solvent to form a reaction mixture, and
stirring the reaction mixture for a reaction under an atmosphere of carbon dioxide gas to obtain the carbon dioxide-reversibly-protected chain extension-crosslinking agent,
wherein the aliphatic diamine is an aliphatic ether diamine.

5. The preparation method according to claim 4, wherein the aliphatic diamine is selected from the group consisting of 2,2'-oxybis(ethylamine), 2,2'-[1,2-ethylenedi(oxy)]bis-ethylamine, 2,2'-[oxybis(2,1-ethyleneoxy)]bis-ethylamine, and 1-(2-aminoethoxy)propan-2-amine.

6. The preparation method according to claim 4, wherein the carbon dioxide gas has a flow rate of 1-20 ml/min.

7. The preparation method according to claim 4, wherein the reaction temperature is 0-35° C.

8. A method for preparing polyurethane elastomer, the method comprising:
step I: adding an oligomeric polyol with a molecular weight of 1000-3000 to a reactor, dewatering it under vacuum, adding a diisocyanate under an inert atmosphere, and heating and reacting the resulting mixture at a temperature of 70-130° C., to obtain a polyurethane prepolymer with an NCO content of 3%-9% as desired;
step II: dispersing carbon dioxide-reversibly-protected chain extension-crosslinking agent according to claim 1 in an organic solvent to obtain a dispersion, then adding the dispersion to the polyurethane prepolymer obtained in step I, mixing them evenly, and then removing the organic solvent to obtain a mixture; and
step III: reacting the mixture obtained in step II at a temperature of 80-200° C. for 5-120 min, curing and molding the mixture to obtain a polyurethane.

9. The method according to claim 8, wherein the oligomeric polyol is one or more selected from the group consisting of a polyester polyol, a polyether polyol, a polycarbonate polyol, and a polymeric polyol.

10. The method according to claim 8, wherein $1 \leq m \leq 5$.

11. The method according to claim 8, wherein $1 \leq m \leq 3$.

12. A method for preparing polyurethane elastomer, the method comprising:
step I: adding an oligomeric polyol with a molecular weight of 1000-3000 to a reactor, dewatering it under vacuum, adding a diisocyanate under an inert atmosphere, and heating and reacting the resulting mixture at a temperature of 70-130° C., to obtain a polyurethane prepolymer with an NCO content of 3%-9% as desired;
step II: dispersing carbon dioxide-reversibly-protected chain extension-crosslinking agent obtained by the preparation method according to claim 4 in an organic solvent to obtain a dispersion, then adding the dispersion to the polyurethane prepolymer obtained in step I, mixing them evenly, and then removing the organic solvent to obtain a mixture; and
step III: reacting the mixture obtained in step II at a temperature of 80-200° C. for 5-120 min, curing and molding the mixture to obtain a polyurethane.

13. The method according to claim 12, wherein the oligomeric polyol is one or more selected from the group consisting of a polyester polyol, a polyether polyol, a polycarbonate polyol, and a polymeric polyol.

14. The method according to claim 12, wherein the aliphatic diamine is selected from the group consisting of 2,2'-oxybis(ethylamine), 2,2'-[1,2-ethylenedi(oxy)]bis-ethylamine, 2,2'-[oxybis(2,1-ethyleneoxy)]bis-ethylamine, and 1-(2-aminoethoxy)propan-2-amine.

15. The method according to claim 12, wherein the carbon dioxide gas has a flow rate of 1-20 ml/min.

16. The method according to claim 12, wherein the reaction temperature is 0-35° C.

* * * * *